(12) United States Patent
Cheng

(10) Patent No.: US 7,282,574 B1
(45) Date of Patent: Oct. 16, 2007

(54) DICHROIC AZO DYESTUFF AND THE POLARIZING FILM MAKING FROM THE SAME

(75) Inventor: Ming-Chin Cheng, Kuanyin Industrial Park (TW)

(73) Assignee: Everlight USA, Inc., Pineville, NC (US)

( * ) Notice: Subject to any disclaimer, the term of this patent is extended or adjusted under 35 U.S.C. 154(b) by 0 days.

(21) Appl. No.: 11/519,062

(22) Filed: Sep. 12, 2006

(30) Foreign Application Priority Data

Feb. 10, 2006 (CN) .................. 2006 1 0007087

(51) Int. Cl.
*C09B 56/06* (2006.01)
*G02B 5/30* (2006.01)
*F21V 9/14* (2006.01)

(52) U.S. Cl. .................. 534/571; 252/585; 359/491
(58) Field of Classification Search ................ 534/571; 252/585; 359/491
See application file for complete search history.

(56) References Cited

U.S. PATENT DOCUMENTS

| | | | | |
|---|---|---|---|---|
| 2,004,250 A | * | 6/1935 | Schindhelm et al. | 534/571 |
| 4,297,278 A | * | 10/1981 | Nickel | 534/571 |
| 5,423,100 A | * | 6/1995 | Misawa et al. | 8/489 |

* cited by examiner

Primary Examiner—Fiona T Powers
(74) Attorney, Agent, or Firm—Bacon & Thomas PLLC

(57) ABSTRACT

The present invention relates to a azo dyestuff compound of the following formula (I), of which the free acid is represented by the following formula:

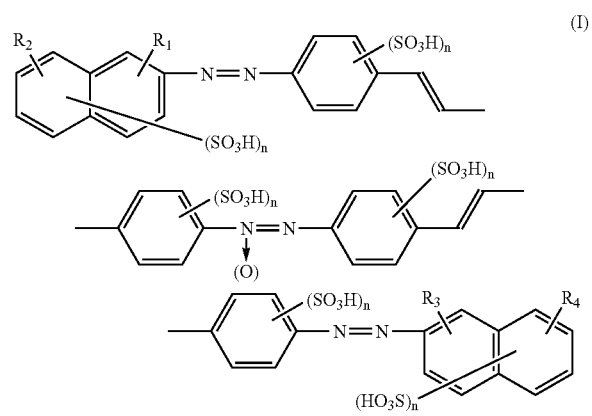

wherein $R_1$, $R_2$, $R_3$, $R_4$, and n are defined as in the specification. The azo dyestuff compound of formula (I) of the present invention is used for preparing polarizing film. The present invention also relates to a polarizing film comprising the azo dyestuff compound of formula (I), which has excellent degree of polarization.

23 Claims, No Drawings

DICHROIC AZO DYESTUFF AND THE POLARIZING FILM MAKING FROM THE SAME

BACKGROUND OF THE INVENTION

1. Field of the Invention

The present invention relates to a novel dichroic azo dyestuff used for a polarizing film and the polarizing film thereof.

2. Description of the Related Art

The current polarizing films are grouped into Ioding Type and Dye Type.

Ioding Type Polarizing Film: the polarizing film constituted with PVA and iodine is the major part of the market. The major disadvantage of Ioding Type Polarizing Film is that the polarized efficiency is reduced within the elapsed time under high temperature and moisture. Although the utilization of boric acid, glyoxal, or heat treatment which can form polyethylene caused by the reduction of OH groups enhances the heat proof character, it is still not met the requirement of heat and moisture proof claimed in some situations.

A direct azo-dye is the major part of the dichroic dyestuff used for Dye Type Polarizing Film. It is the characteristic that the axial in the structure of the dye molecule is linear. Thereby, the dichroic property is presented due to the difference between the absorbance of the molecule with the parallel and perpendicular axial to light.

Dye Type Polarizing Film: a dye type polarizing film, with preferred heat proof, moisture proof and so on, is usually used for the outdoor type displays necessary for cars, airplanes and so on. However, the major disadvantage is the low polarized efficiency. The manufacturing method, through the stretching alignment of PVA and the dyes with identical absorbance and high-polarized efficiency in visible light, is the same as that of Ioding Type Polarizing Film. Generally, the direct dyes or acid dyes with azo groups are used. As compared with Ioding Type, Dye Type has preferred heat and moisture stability. In other words, it has preferred heat and moisture proof.

The present invention displays that the derivation from the core structure of the azoxy type polarizing film to establish side chains can provide high-polarized efficiency and climate proof. The purity of the easily afforded dyestuff by less synthetic steps is preferred, without complicated purification. The PVA type polarizing film of the dyestuff has preferred heat and moisture proof and its polarized efficiency is equal to that of Ioding Type Polarizing Film.

SUMMARY OF THE INVENTION

The present invention provides a dichroic azo dyestuff with heat proof and moisture proof characters. The present invention also provides a dye type polarizing film.

The dichroic azo dyestuff of the present invention, of which the structure of the free acid is the azo dyestuff compound of the following formula (I):

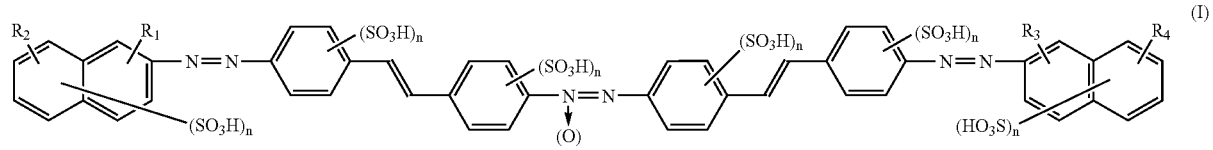

wherein, $R_1$ and $R_3$ each independently is —OH or —NH$_2$;

$R_2$ and $R_4$ each independently is —H, —OH, —NH$_2$ or —NHR$_5$;

$R_5$ is

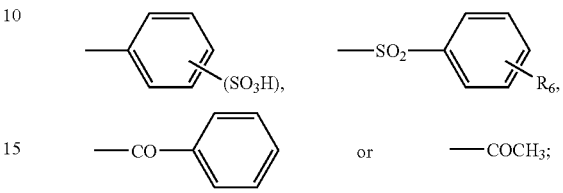

$R_5$ is $R_6$ is —H or —CH$_3$;

n is 0, 1 or 2.

The azo dyestuff compound of formula (I) of the present invention, where, preferably, n is 1 or 2; $R_1$ is —OH; and $R_3$ is —NH$_2$.

Examples of the azo dyestuff compound of formula (I) of the present invention includes the azo dyestuff compounds of the following formula (1) to (12):

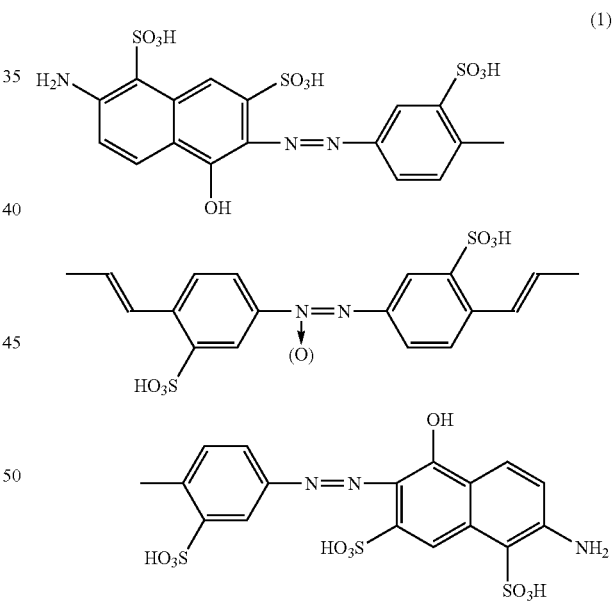

-continued
(2)
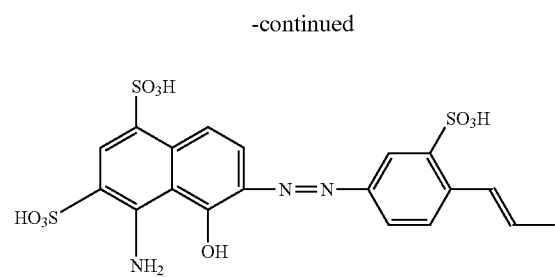
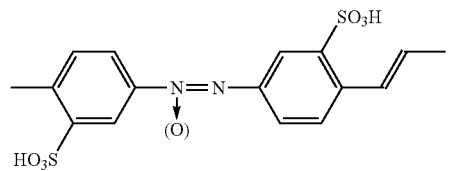
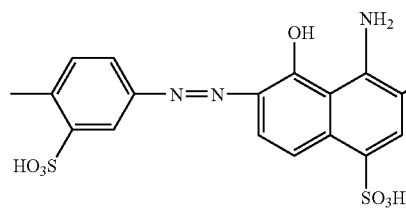
(3)
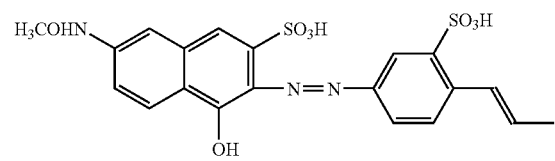
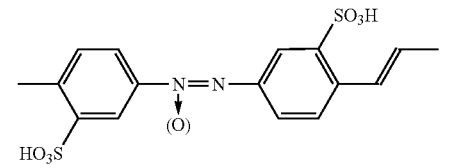
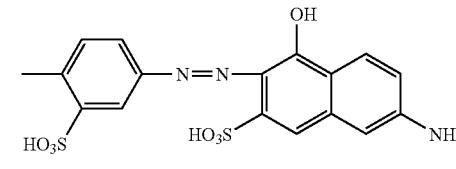
(4)
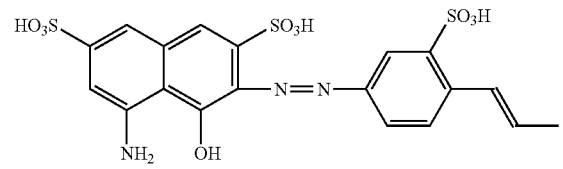
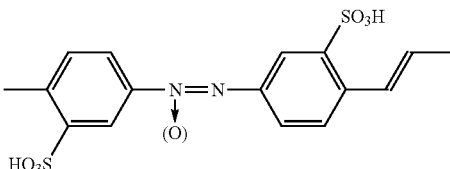
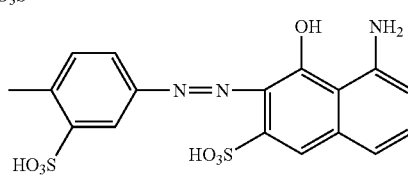
-continued
(5)
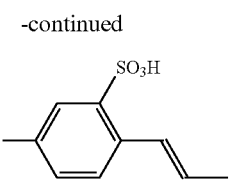
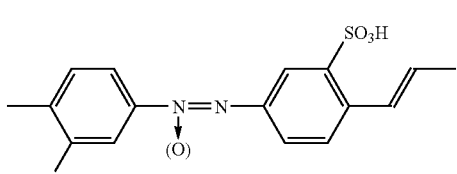
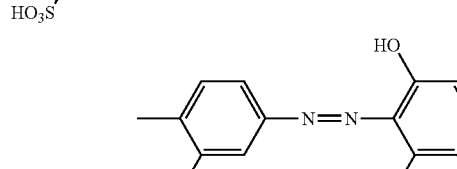
(6)
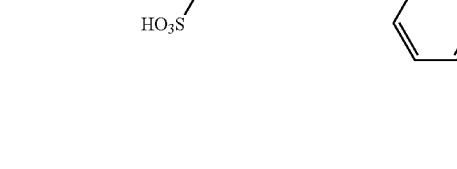
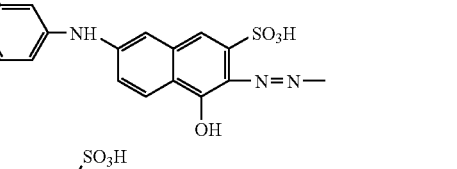
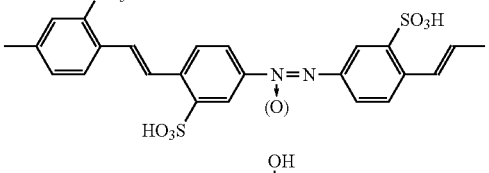
(7)
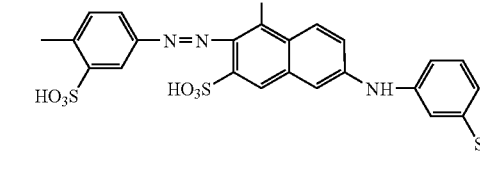
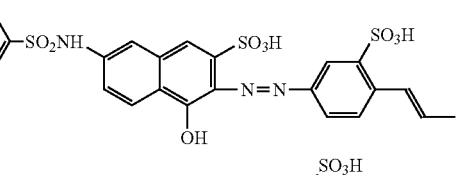
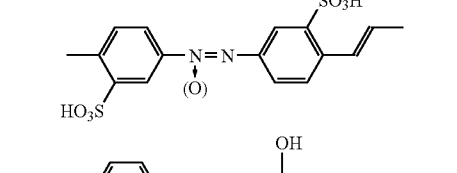
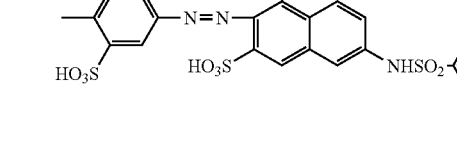

-continued

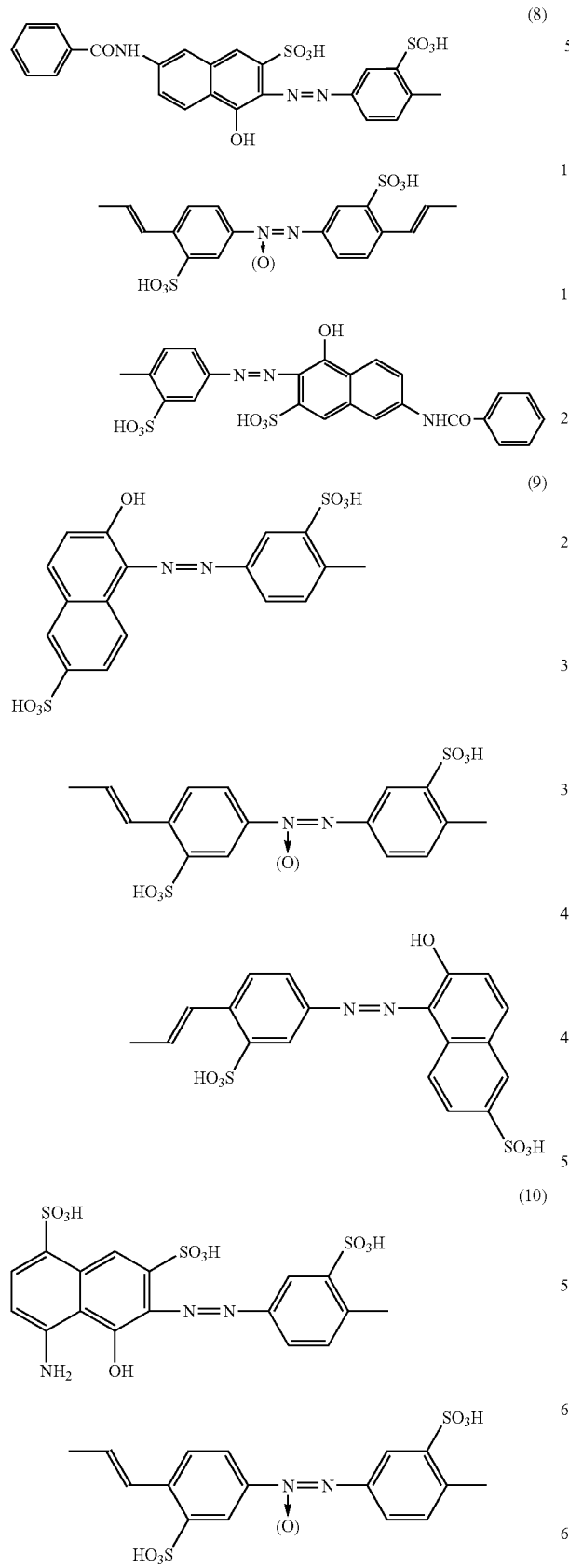

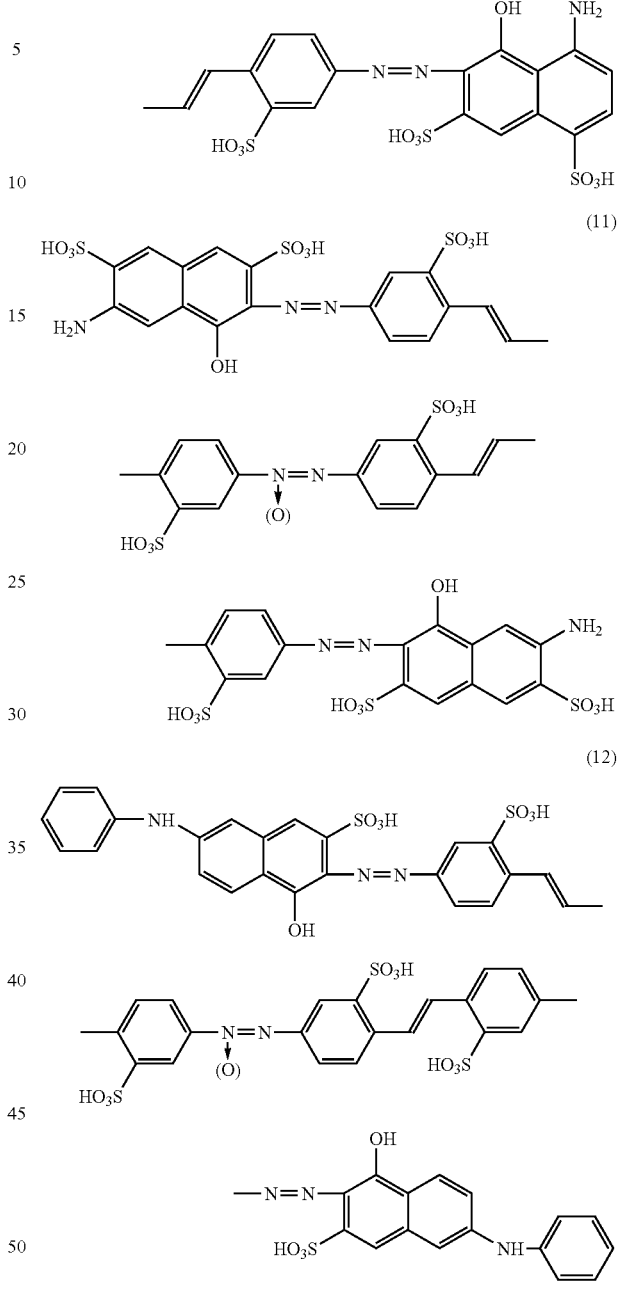

The dye type polarizing film of the present invention is made from polarizing film base material containing dichroic dyestuff, said dichroic dyestuff comprising the above-mentioned azo dyestuff compound of formula (I).

The dye type polarizing film of the present invention, wherein the polarizing film base material is preferable polyvinyl alcohol.

The dye type polarizing film of the present invention, wherein, the azo dyestuff compound comprised in the dichroic dyestuff can be any of the above-mentioned formulas (1) to (12).

DETAILED DESCRIPTION OF THE PREFERRED EMBODIMENT

The azo dyestuff compound of formula (I) of the present invention can be presented in forms of free acid or salt, such as alkaline metal salt and alkaline-earth metal salt in particular, and the alkaline metal salt is preferred in use.

The general synthesis equation of the azo dyestuff compound of formula (I) of the present invention is described as below:

1. Diazotization:

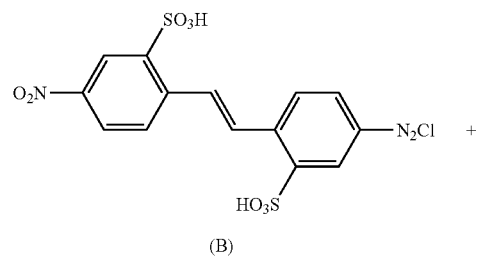

2. Coupling Reaction

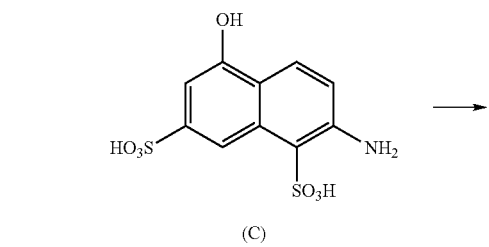

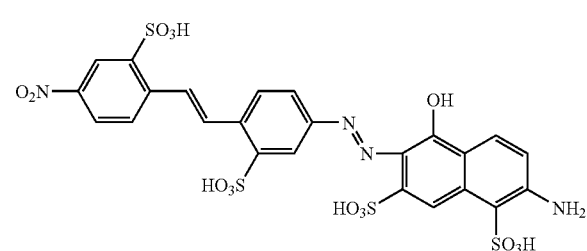

3. Semi-Reduction:

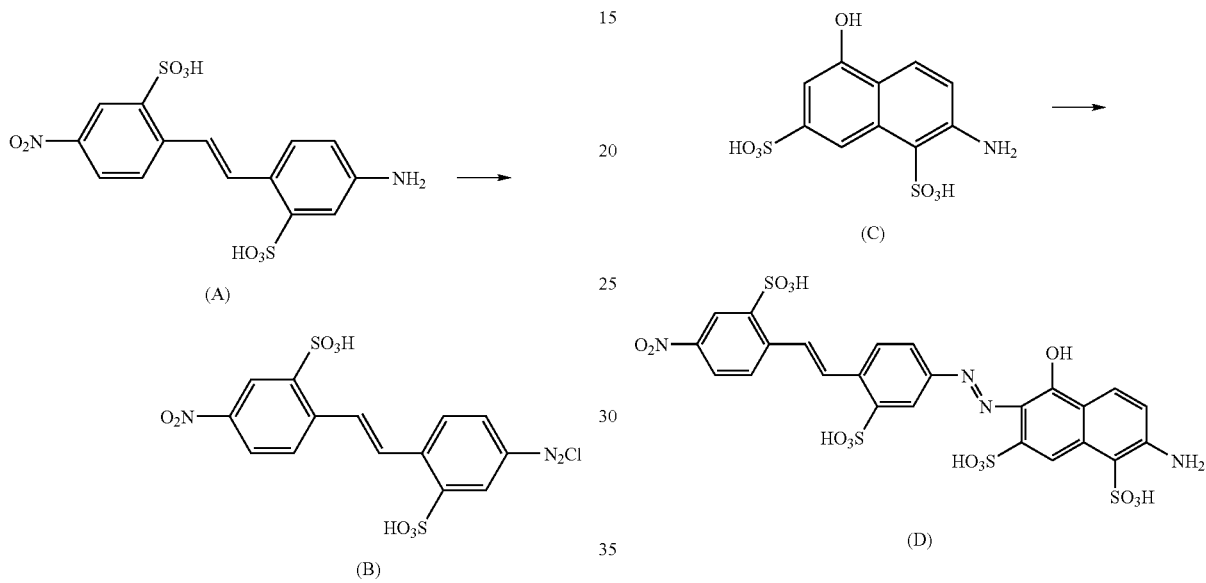

Equation (I)

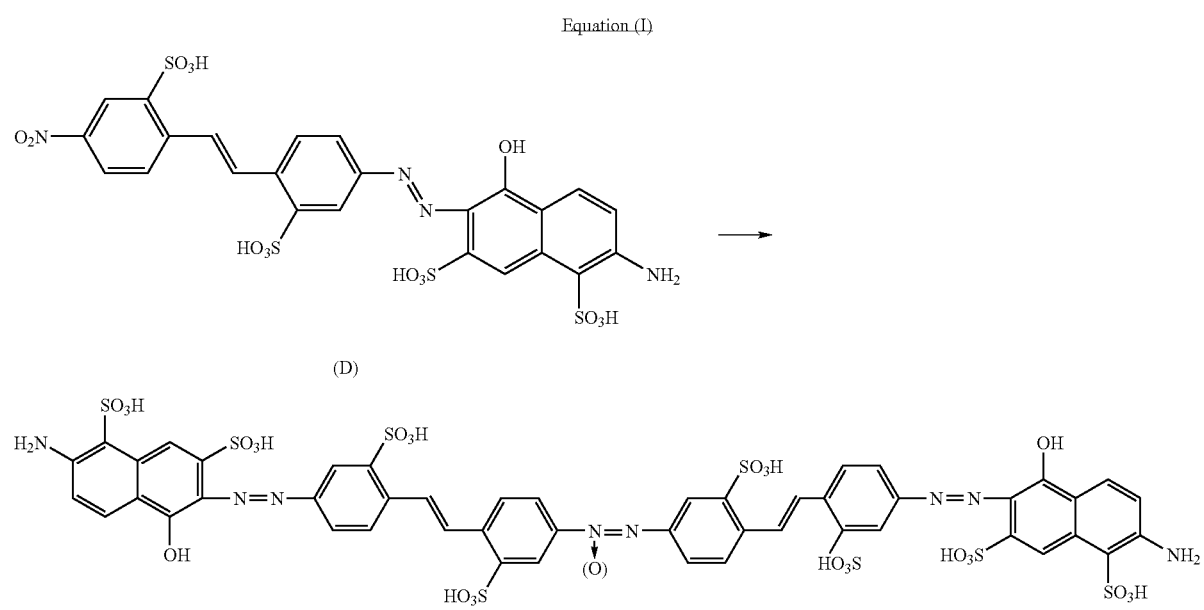

The azo dyestuff compound of formula (I) of the present invention can be synthesized with the above steps.

The azo dyestuff compound of formula (I) of the present invention can be in forms of free acids or salts. Examples of salts include alkaline metal salts, such as lithium salt, sodium salt, sylvite; ammonium salt; organic ammonium salt, such as ethanolamine salt and alkylammonium. It is better to take sodium salt while using the compound in polarizing film.

The preparation of the dye type polarizing film of the present invention, according to conventional dyeing method, is to contain the polymer film as polarizing film base material with the dyestuff compound of formula (I). Besides, the dyestuffs can work with organic dyestuffs other then the compound of formula (I) to achieve customers' needs.

The polymer film of the polarizing film base material comprises materials made from polyvinyl alcohol resin, polyvinyl acetate resin, ethylene/vinylacetate (EVA) resin, nylon resin, and polyester resin.

For the adsorption performance and dyestuff directionality performance of the polarizing film base material, the film derived from polyvinyl alcohol compound (especially polyvinyl alcohol film) is preferred.

Generally, a conventional method of dyeing the polymer film is taken to prepare the polarizing film. The dyeing method, for example, can be carried out with the following steps. Firstly, dissolve dichromatic dyestuffs in water to obtain a dyeing solution. The concentration of the dyestuffs in the dyeing solution is not limited, but usually in the range of 0.0001-10% by weight. Besides, a dyeing auxiliary agent can be added if necessary. Take sodium sulfate for example, it is appropriate to add 1-10% by weight in the dyeing solution.

The polymer film is dyed by dipping into the above dyeing solution. The temperature of dyeing is preferable 40° C.-80'. Stretching the polymer film to make the dichroic dyestuff have directionality. The stretching method can be any conventional methods, such as wet method and dry method, to let the polymer film have directionality before or after dyeing.

A post-treatment to the dichromatic dyestuff-contained and directional polymer film can be taken, if desired, such as treated with boric acid according to conventional methods. The purpose of such a post-treatment is to improve the transmission, light polarization and durability of the polarizing film. The adequate condition of boric acid treatment depends on the type of the polymer film. The concentration of boric acid in the boric acid solution is usually in the range of 1-15% by weight, preferably 5-10% by weight, and the temperature ranges from 30° C. to 80° C., preferably 50° C. to 80° C.

In addition, the retention process can be preformed by the solution including cationic polymers if necessary. The polarizing plate can be formed by making the protecting film of high light transmittance and mechanic strength adhere to the one or both surface of the polarizing film constituted with the dyestuff afforded through the above method. The material of the protecting film could be that in common use, including cellulose acetate films, acrylic acid films and fluoro resin films (for examples: perfluorinated ethvlence-propylene copolymers, polyester films, polyolefine cigarette films, polyamide films).

The color can be modified or the polarized efficiency can be improved by other organic dyes worked with the dichroic azo dyestuff of formula (I) used for the polarizing film. Herein, the organic dyes can be any dyes with the high dichroic character.

For convenience, the following embodiments are used for the further concrete description.

The following embodiments are the description of the present invention, and the claims of the present invention are not limited to these.

Unless otherwise stated, the "° C." used in the examples refers to temperature, the parts of weight and volume are in "g" and "ml", respectively.

EXAMPLE 1

Preparing the Azo-Dyestuff Compound of Formula (1):

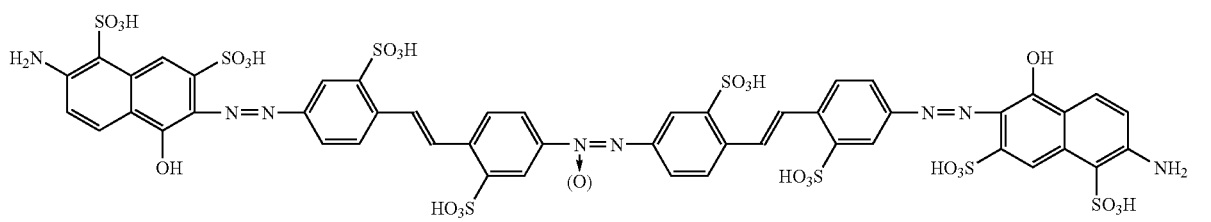

(1)

The above azo-dyestuff compound of formula (1) can be obtained, according to the following three steps:

1. DiDiazotization:

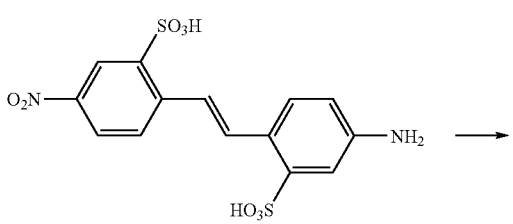

(A)

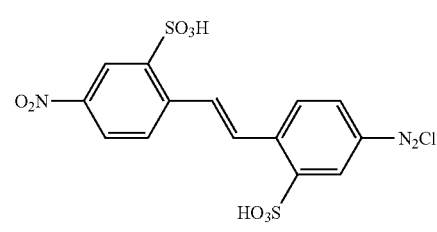

(B)

40 parts of 4-amino-4'-nitrostilbene-2,2'-disulfonic acid (A) was dissolved in 300 parts of water and 30 parts of 32% hydrochloride acid was added, followed by stirring at 0-5° C. Diazotization was realized with the addition of 8 parts of sodium nitrite at the same temperature range.

2. Coupling Reaction:

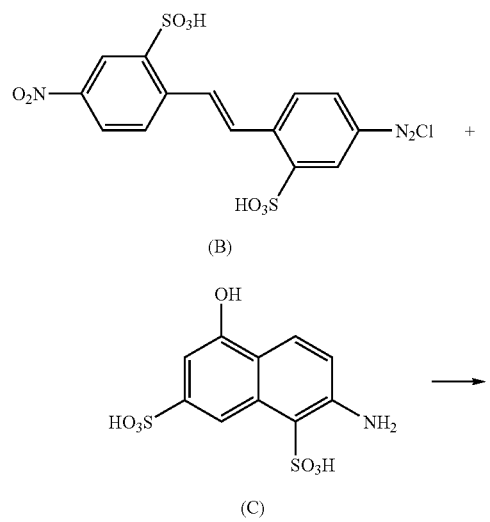

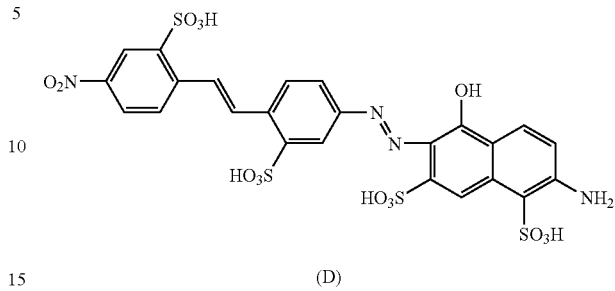

-continued 35.12 parts of 2-amino-5-hydroxynaphthalene-1,7-disulfonic acid (C) was dissolved in the mixture of 200 parts of cool water and 35 parts of sodium carbonate, to which the above reagent (B) from Diazotization was then added dropwise. Thereby, the coupling reaction was realized. After the reaction was completed, the monoazo compound of free acid (D) was obtained by filtration.

3. Semi-Reduction:

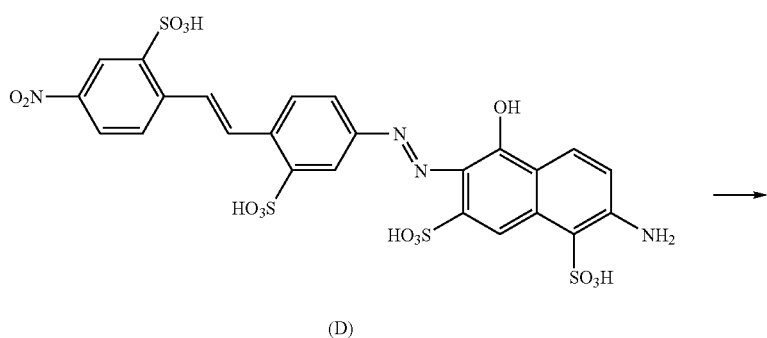

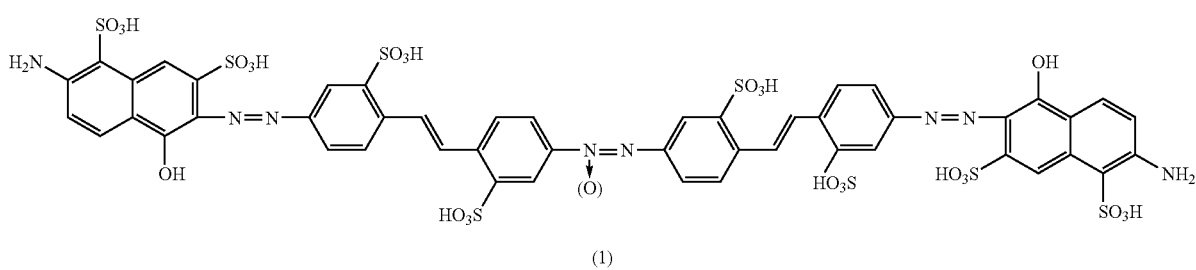

The monoazo compound (D) was dissolved in 400 parts of water, followed by the addition of sodium hydroxide solution until the solution was strong basic. Reduction was realized with the addition of 8 parts of glucose at 40° C. After the reaction was completed, pH was adjusted to 7.0 and then filtration. The compound of free acid of formula (1), with λ max at 530 nm in water, was obtained.

EXAMPLES 2 TO 12

Repeat the reaction steps of Example 1, but the 2-amino-5-hydroxynaphthalene-1,7-disulfonic acid of reactant (C) is replaced with the following reactant (C) as shown in Table 1. After completed the reaction, the reaction solution are filtered and dried to obtain the products of formula (2) to formula (12) as shown in Table 1. The λ max of the compounds of formula (2) to formula (12) in water were presented in Table 1.

TABLE 1

| Example | Reagent (C) | Product | λ max |
|---|---|---|---|
| 1 | (structure: naphthalene with OH, HO$_3$S, NH$_2$, SO$_3$H) | Formula (1) | 530 nm |
| 2 | (structure: naphthalene with OH, NH$_2$, SO$_3$H, SO$_3$H) | Formula (2) | 600 nm |
| 3 | (structure: naphthalene with OH, HO$_3$S, NHCOCH$_3$) | Formula (3) | 538 nm |
| 4 | (structure: naphthalene with OH, NH$_2$, HO$_3$S, SO$_3$H) | Formula (4) | 600 nm |
| 5 | (structure: naphthalene with HO, SO$_3$H, SO$_3$H) | Formula (5) | 555 nm |
| 6 | (structure: naphthalene with OH, HO$_3$S, NH-phenyl-SO$_3$H) | Formula (6) | 575 nm |

TABLE 1-continued

| Example | Reagent (C) | Product | λ max |
|---|---|---|---|
| 7 | [structure: 1-hydroxy-naphthalene with HO₃S and NHSO₂-phenyl] | Formula (7) | 532 nm |
| 8 | [structure: 1-hydroxy-naphthalene with HO₃S and NHCO-phenyl] | Formula (8) | 522 nm |
| 9 | [structure: 6-hydroxy-naphthalene-2-sulfonic acid] | Formula (9) | 532 nm |
| 10 | [structure: 1-amino-8-hydroxy-naphthalene-3,6-disulfonic acid derivative] | Formula (10) | 585 nm |
| 11 | [structure: 3-amino-5-hydroxy-naphthalene-2,7-disulfonic acid] | Formula (11) | 585 nm |
| Example 12 | [structure: 1-hydroxy-6-anilino-naphthalene-3-sulfonic acid] | Formula (12) | 540 nm |

The following is the structure of formula (1) to (12) compounds

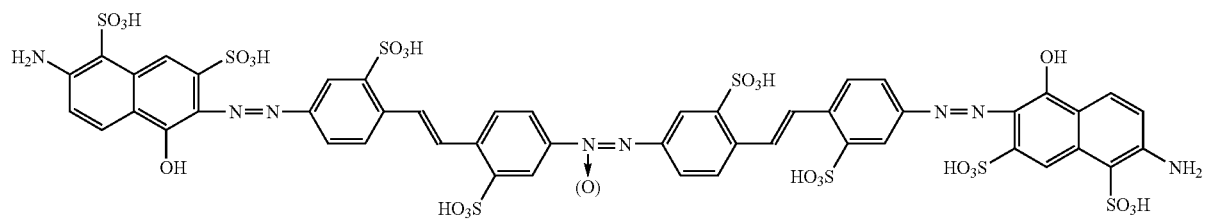

(1)

-continued
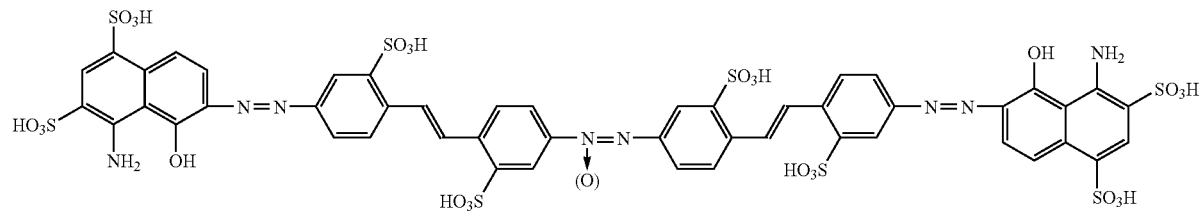
(2)
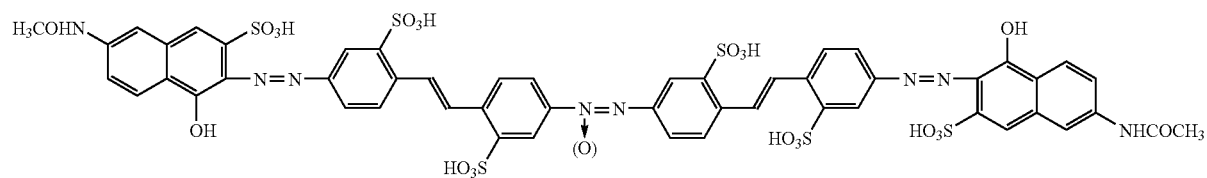
(3)
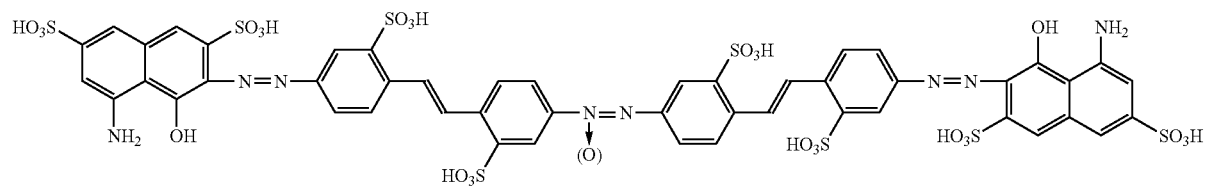
(4)
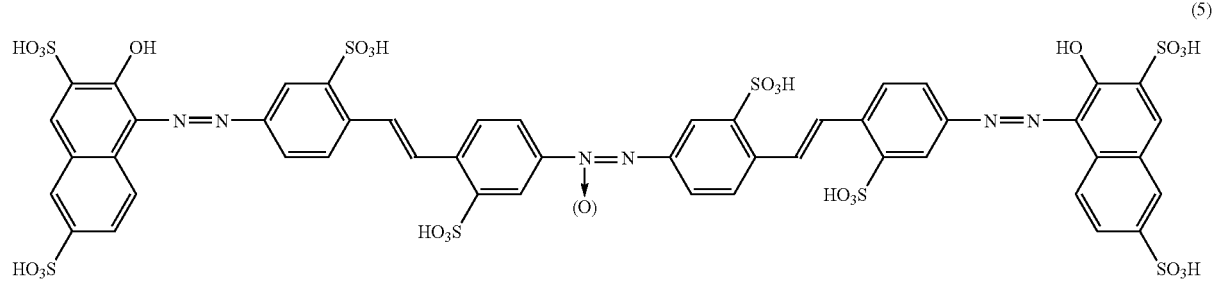
(5)
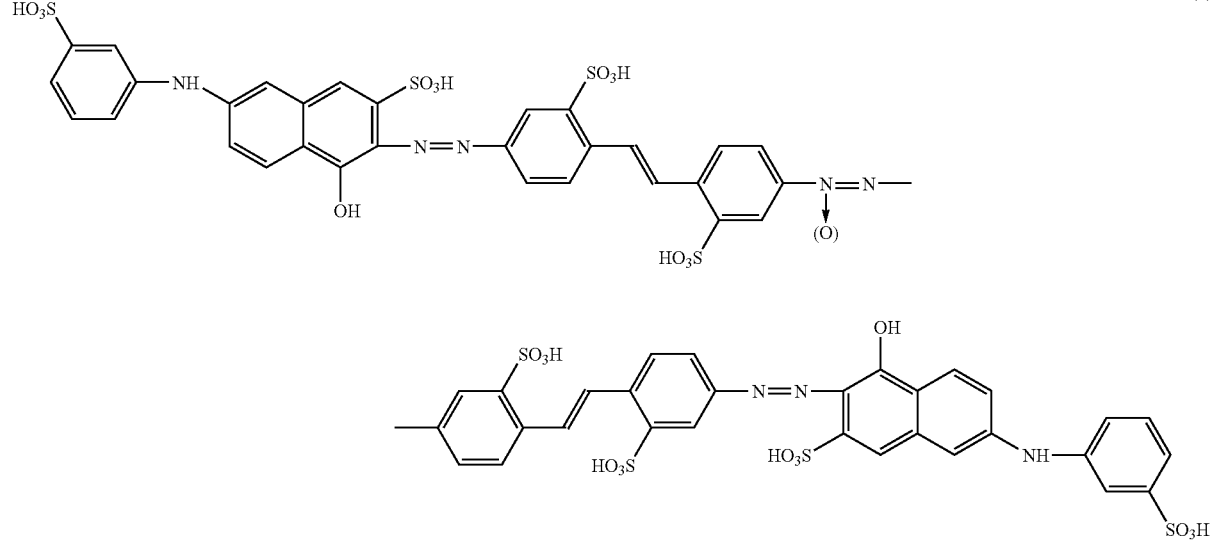
(6)

-continued
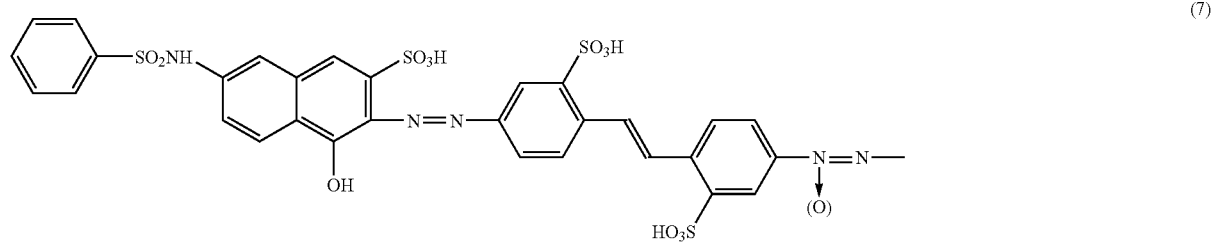
(7)
(8)
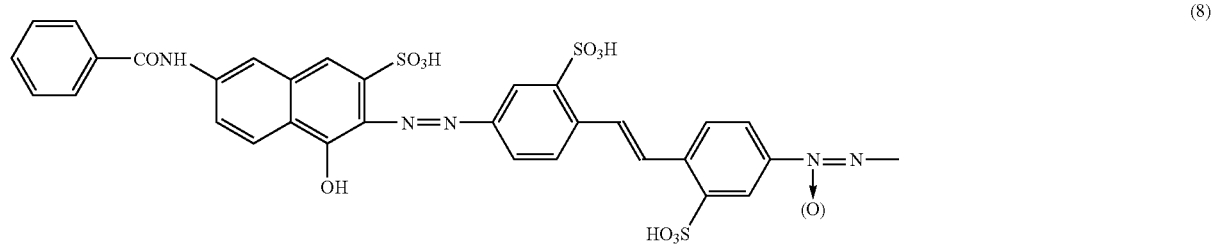
(9)
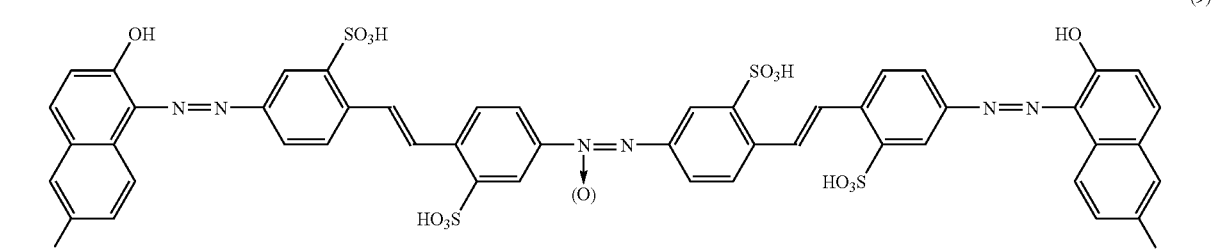
(10)
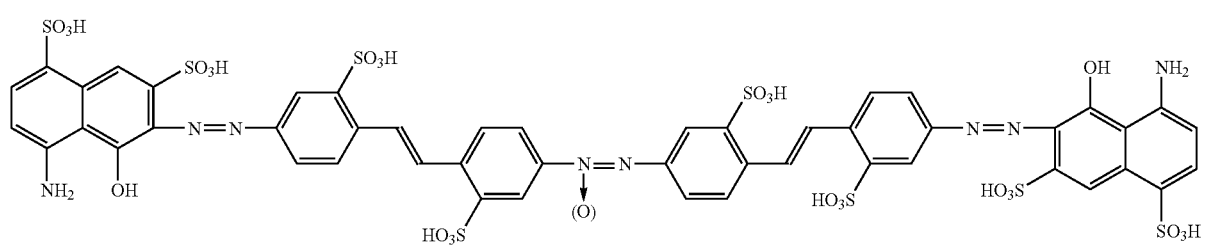
(11)
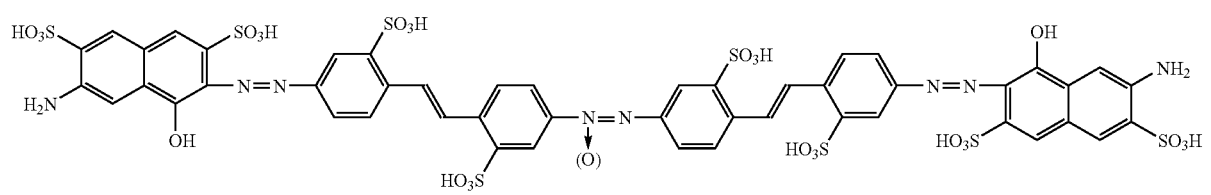

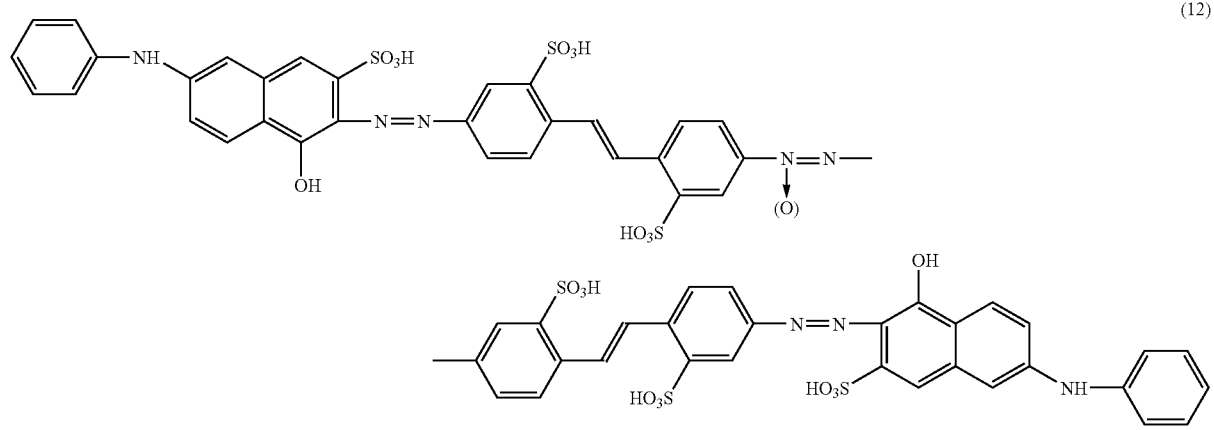

The following Examples 13 to 24 are related to the preparation of the dye type polarizing films of the present invention and the measurement of light polarization.

According to Example 13 to 24, the polarizing films can be formed from the obtained dyes in Examples 1 to 12, with which other dyes work or not. In the following Examples, UV-2550 UV-VISIBLE of SHIMADZU was used for the measurement.

"T" is the light transmittance at one wavelength; "Ts" is the light transmittance of one polarizing film.

T parallel: the light transmittance of two polarizing films overlapping each other in the same direction. It is called "parallel light transmittance".

T cross: the light transmittance of two polarizing films cross-overlapping each other perpendicularly. It is called "cross light transmittance".

"V" is the value from the calculation according to the following equation where T parallel and T cross is measured at λ max:

$V=(\sqrt{((T\ parallel - T\ cross)/(T\ parallel + T\ cross))})\times 100$

EXAMPLE 13

The polyvinyl alcohol film of 75 μm thickness, Kuraray vinylon 7500 made from Kuraray, was stretched five-fold longer in one vertical direction and the base material of the polarizing film was obtained. The polyvinyl alcohol film in strain form was dipped in the 65° C. solution of 0.025% azo compound of formula (1) made from Example 1 and 2.0% sodium sulfate (served as a dyeing agent). Then, the film was dipped in 7.5% boric acid at 65° C. for five minutes, followed by taking out the film. The polarizing film was obtained after it washed with 20° C. water for 20 seconds and dried at 50° C. The characteristics of the polarizing film are V=99.97 and Ts=45.07. The polarizing film with high-polarized efficiency does not discolor under the high-temperature and high-moisture condition.

EXAMPLE 14 TO 24

The same steps as Example 13 obtained the polarizing films with the azo-dyestuff compounds of formula (2) to (12), replacing formula (1) in Example 13. Herein, the polarizing films constituted from the azo-dyestuff of formula (2) to (12) in Table 2 were obtains. The light polarization character of the dye type polarizing films was presented in Table 2.

TABLE 2

The polarization character of the polarizing films

| Example | Polarizing film of azo-dyestuff | λ max | V | Ts |
|---|---|---|---|---|
| 13 | Polarizing film of formula (1) | 530 nm | 99.97 | 45.07 |
| 14 | Polarizing film of formula (2) | 600 nm | 99.57 | 45.53 |
| 15 | Polarizing film of formula (3) | 538 nm | 99.97 | 46.21 |
| 16 | Polarizing film of formula (4) | 600 nm | 99.61 | 45.45 |
| 17 | Polarizing film of formula (5) | 555 nm | 98.74 | 43.28 |
| 18 | Polarizing film of formula (6) | 575 nm | 99.11 | 45.18 |
| 19 | Polarizing film of formula (7) | 532 nm | 99.84 | 45.30 |
| 20 | Polarizing film of formula (8) | 522 nm | 99.00 | 43.65 |
| 21 | Polarizing film of formula (9) | 532 nm | 99.04 | 38.56 |
| 22 | Polarizing film of formula (10) | 585 nm | 99.12 | 46.52 |
| 23 | Polarizing film of formula (11) | 585 nm | 99.56 | 41.32 |
| 24 | Polarizing film of formula (12) | 540 nm | 99.90 | 42.43 |

According to the result of the measurement in the above table, the polarizing films with the azo dyestuff compounds in the present invention exhibit high-polarized efficiency.

From the foregoing description, regardless of the objects, the techniques, the effects or the skill aspects and developments, the present invention is distinctive with respect to known skills. Although the present invention has been explained in relation to its preferred embodiment, it is to be understood that many other possible modifications are variations can be made without departing from the scope of the invention as hereinafter claimed.

23. The dye type polarizing film of claim 13, wherein said azo dyestuff compound of formula (I) is the azo dyestuff compound of the following formula (11):
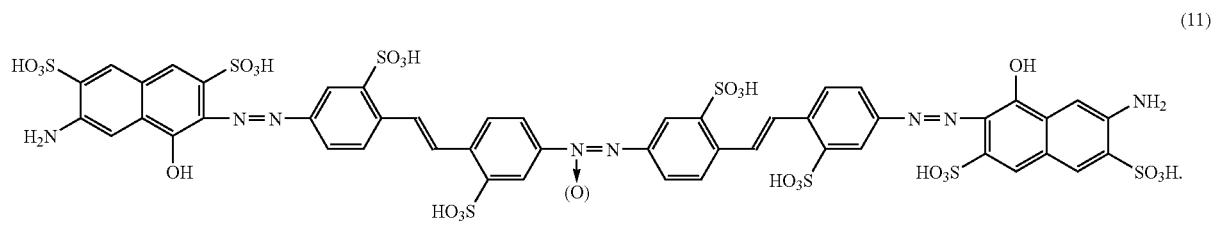

What is claimed is:

1. An azo dyestuff compound of the following formula (I), of which the free acid is represented by the following formula:

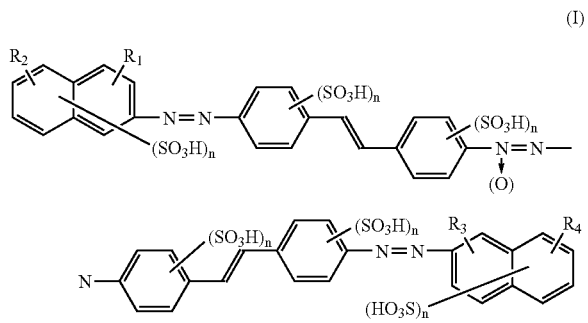

wherein, $R_1$ and $R_3$ each independently is —OH or —NH$_2$;

$R_2$ and $R_4$ each independently is —H, —OH, —NH$_2$ or —NHR$_5$;

$R_5$ is

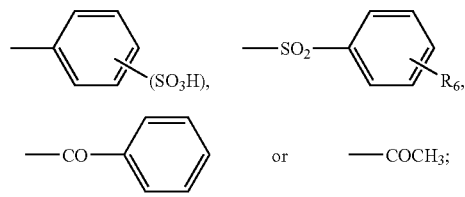

$R_6$ is —H or —CH$_3$;

n is 0, 1 or 2.

2. The azo dyestuff compound of claim 1, wherein said n is 1 or 2.

3. The azo dyestuff compound of claim 1, wherein $R_1$ is —OH, and $R_3$ is —NH$_2$.

4. The azo dyestuff compound of claim 1, wherein the formula (I) compound is the following formula (1) compound:

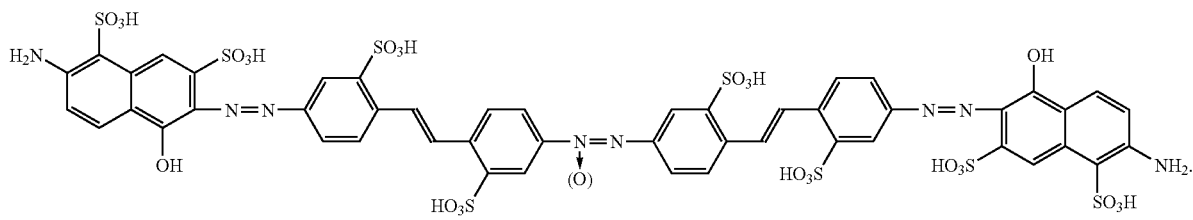

5. The azo dyestuff compound of claim 1, wherein the formula (I) compound is following formula (2) compound:

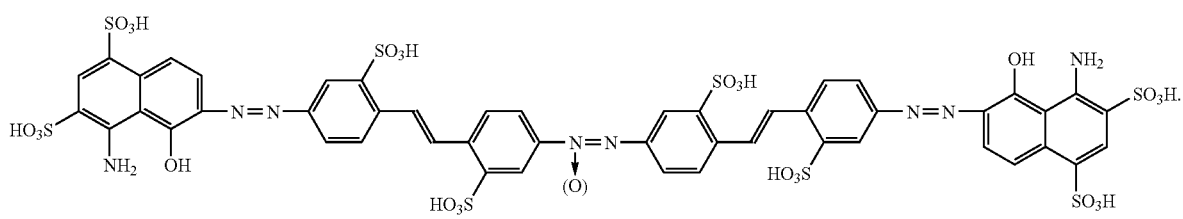

6. The azo dyestuff compound of claim 1, wherein the formula (I) compound is the following formula (3) compound:

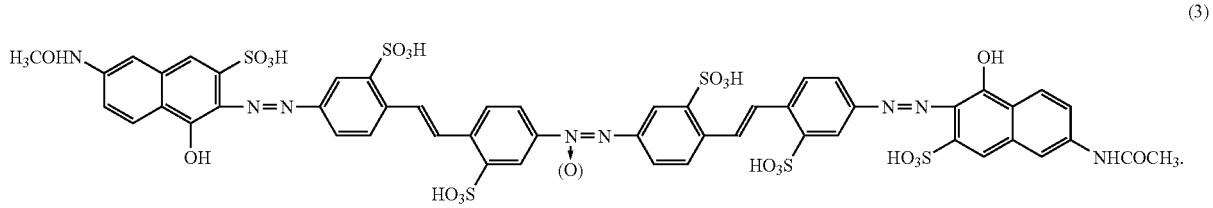

7. The azo dyestuff compound of claim 1, wherein the formula (I) compound is the following formula (4) compound:

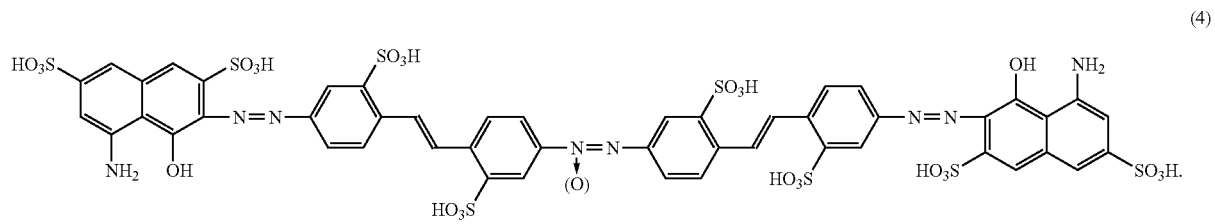

(4)

8. The azo dyestuff compound of claim 1, wherein the formula (I) compound is the following formula (6) compound:

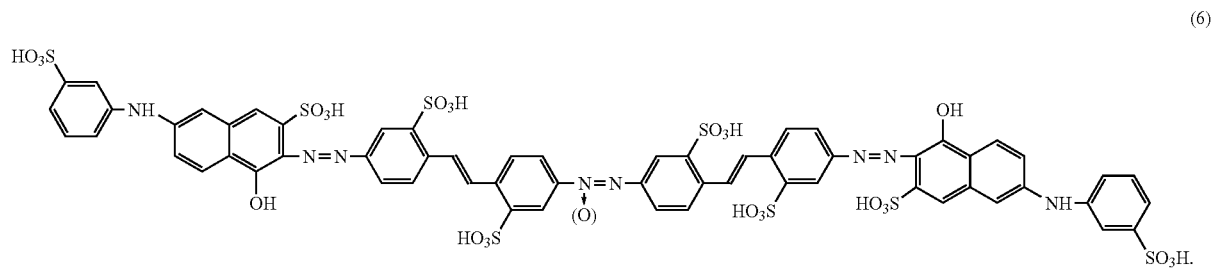

(6)

9. The azo dyestuff compound of claim 1, wherein the formula (I) compound is the following formula (7) compound:

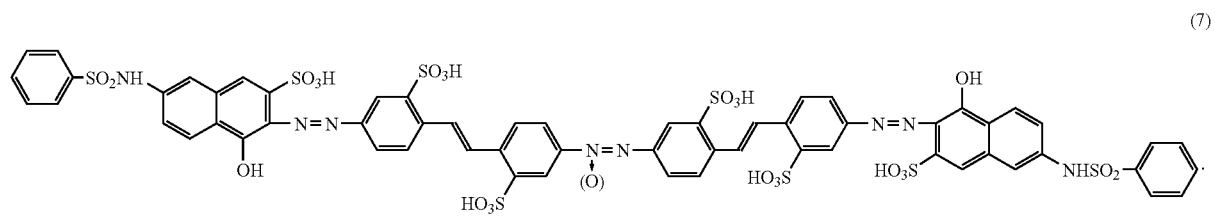

(7)

10. The azo dyestuff compound of claim 1, wherein the formula (I) compound is the following formula (8) compound:

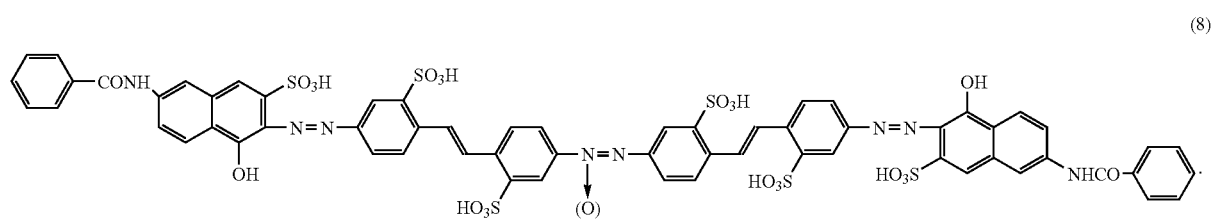

(8)

11. The azo dyestuff compound of claim 1, wherein the formula (I) compound is the following formula (10) compound:

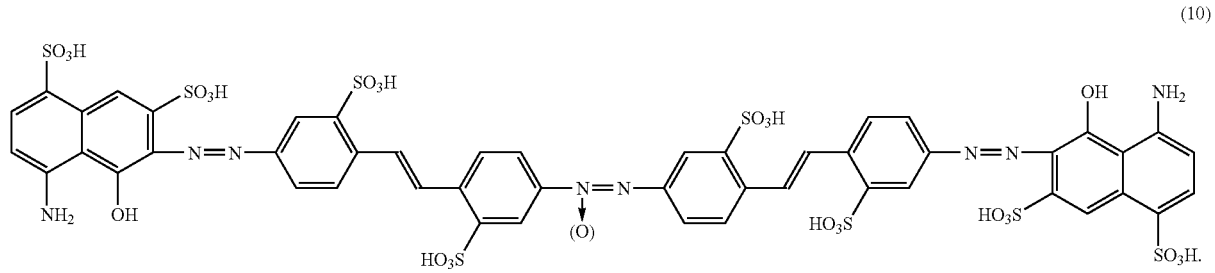

(10)

12. The azo dyestuff compound of claim 1, wherein the formula (I) compound is the following formula (11) compound:

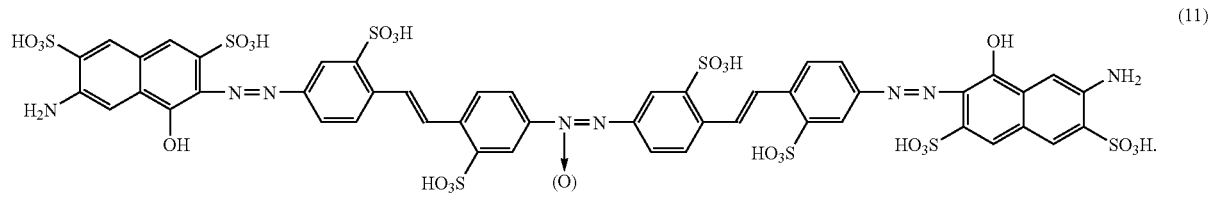

(11)

13. A dye type polarizing film, said film is made from a polarizing film base material containing dichroic dyestuff, said dichroic dyestuff comprising the azo dyestuff compound of the following formula (I), of which the free acid is represented by the following formula:

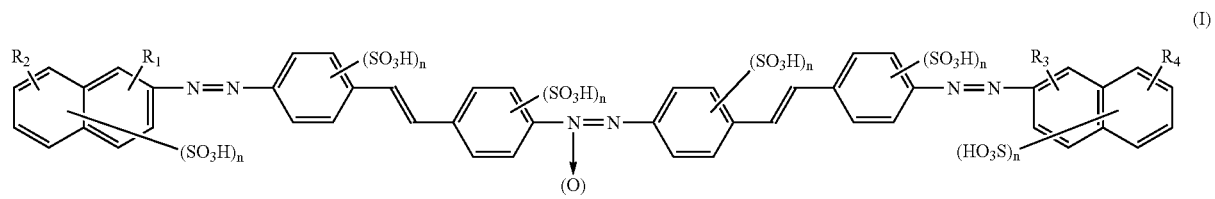

(I)

wherein, $R_1$ and $R_3$ each independently is —OH or —NH$_2$;

$R_2$ and $R_4$ each independently is —H, —OH, —NH$_2$ or —NHR$_5$;

$R_5$ is

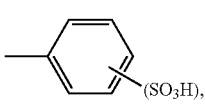 , 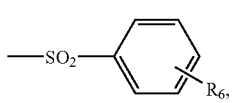 ,

-continued

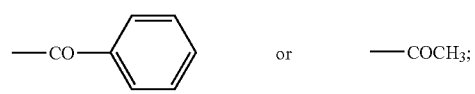 or —COCH$_3$;

$R_6$ is —H or —CH$_3$;

n is 0, 1 or 2.

14. The dye type polarizing film of claim 13, wherein said polarizing film base material is polyvinyl alcohol.

15. The dye type polarizing film of claim 13, wherein said azo dyestuff compound of formula (I) is the azo dyestuff compound of the following formula (1):

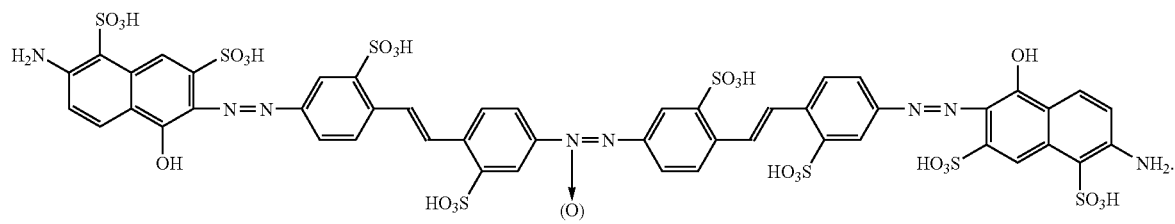

(1)

16. The dye type polarizing film of claim 13, wherein said azo dyestuff compound of formula (I) is the azo dyestuff compound of the following formula (2):

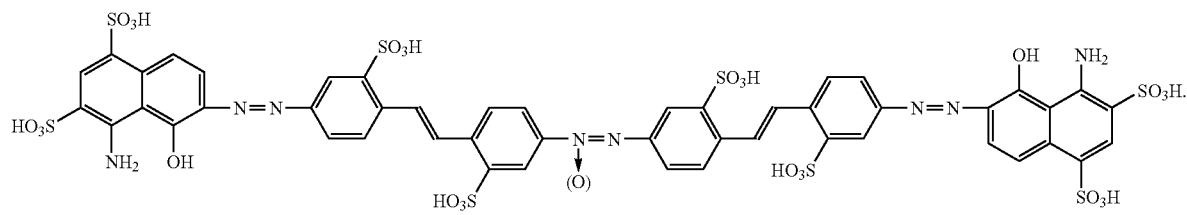

(2)

17. The dye type polarizing film of claim 13, wherein said azo dyestuff compound of formula (I) is the azo dyestuff compound of the following formula (3):

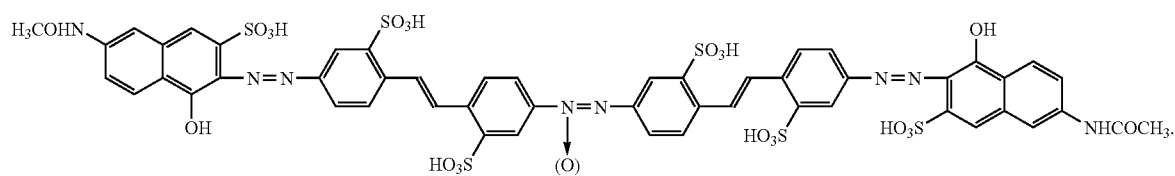

(3)

18. The dye type polarizing film of claim 13, wherein said azo dyestuff compound of formula (I) is the azo dyestuff compound of the following formula (4):

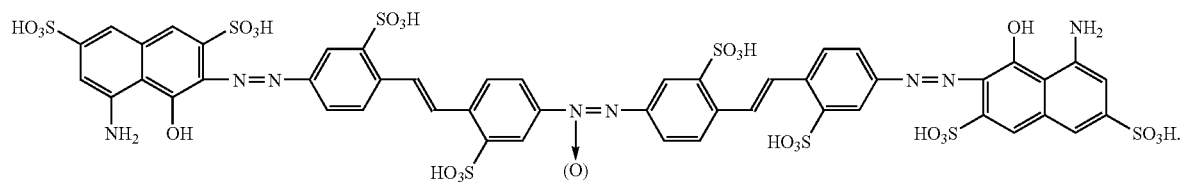

(4)

19. The dye type polarizing film of claim 13, wherein said azo dyestuff compound of formula (I) is the azo dyestuff compound of the following formula (6):

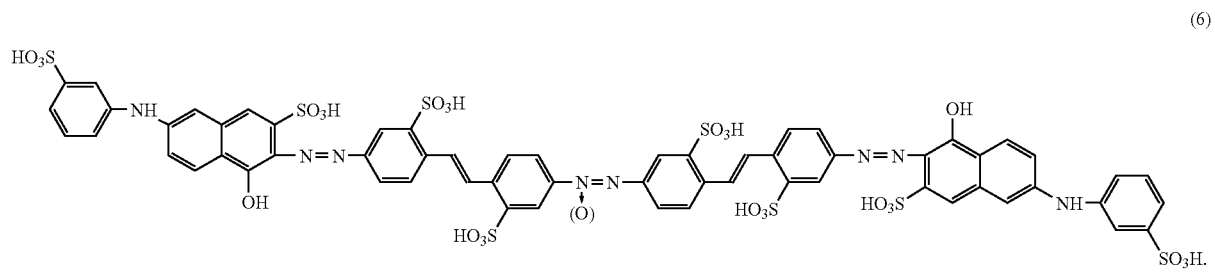

(6)

20. The dye type polarizing film of claim 13, wherein said azo dyestuff compound of formula (I) is the azo dyestuff compound of the following formula (7):

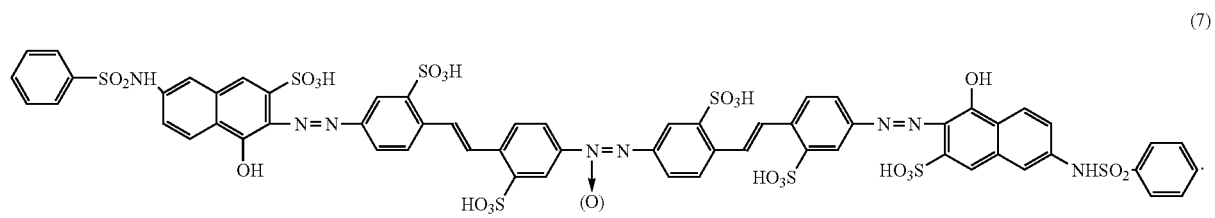

(7)

21. The dye type polarizing film of claim 13, wherein said azo dyestuff compound of formula (I) is the azo dye stuff compound of the following formula (8):

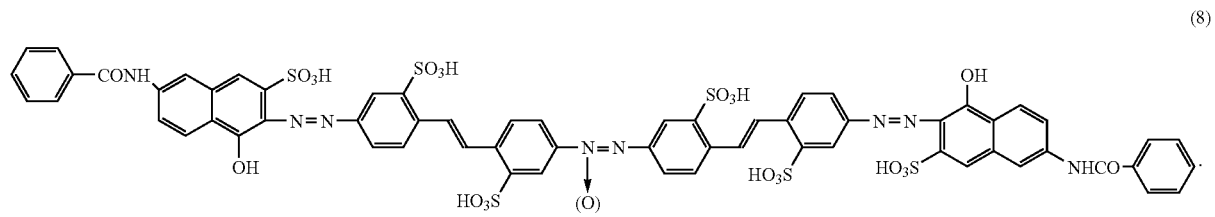

(8)

22. The dye type polarizing film of claim 13, wherein said azo dyestuff compound of formula (I) is the azo dyestuff compound of the following formula (10):

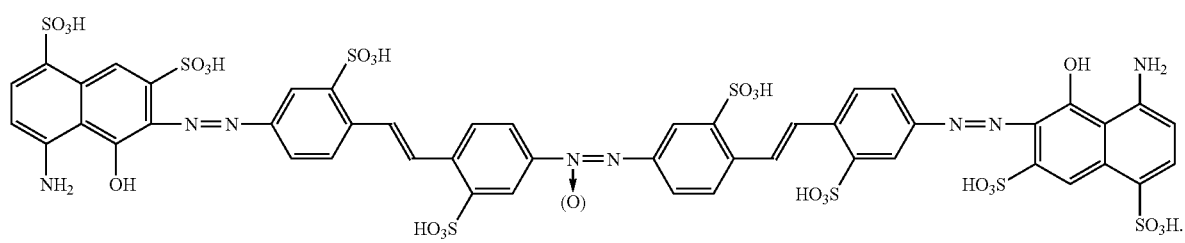

(10)